(12) United States Patent
Moll

(10) Patent No.: US 8,115,932 B2
(45) Date of Patent: Feb. 14, 2012

(54) METHODS AND APPARATUS FOR MEASURING ION IMPLANT DOSE

(75) Inventor: Johannes Moll, Corning, NY (US)

(73) Assignee: Corning Incorporated, Corning, NY (US)

( * ) Notice: Subject to any disclaimer, the term of this patent is extended or adjusted under 35 U.S.C. 154(b) by 440 days.

(21) Appl. No.: 12/473,896

(22) Filed: May 28, 2009

(65) Prior Publication Data

US 2010/0302547 A1  Dec. 2, 2010

(51) Int. Cl.
*G01N 21/55* (2006.01)
*H01L 21/425* (2006.01)

(52) U.S. Cl. ........ 356/448; 438/514; 356/320; 356/369; 356/390; 356/445

(58) Field of Classification Search .................. 356/445, 356/448
See application file for complete search history.

(56) References Cited

U.S. PATENT DOCUMENTS

| | | | |
|---|---|---|---|
| 5,978,074 A | 11/1999 | Opsal et al. | 356/72 |
| 6,323,951 B1 | 11/2001 | Borden et al. | 356/502 |
| 6,426,644 B1 | 7/2002 | Borden et al. | 324/765 |
| 6,483,594 B2 | 11/2002 | Borden et al. | 356/502 |
| 6,535,285 B1 | 3/2003 | Opsal et al. | 356/369 |
| 7,078,711 B2 | 7/2006 | Borden | 250/492.21 |
| 2005/0112853 A1 | 5/2005 | Kuzbyt et al. | 438/514 |

OTHER PUBLICATIONS

Ray Kuzbyt, et al "Advances in optical Densitometry for Low dose Measurement," 2002 IEEE p. 240-243.
Sing, et al "Low and High Dose Process Monitoring using the BX-10 Implant Monitor System," 2000 IEEE p. 639-641.
A.K. Hochberg, "Measurement of Ion Implantation Doses in Silicon by Ellipsometry and Spectral Reflectance," *ASTM Special Technical Publication—Silicon Processing*, Jan. 1, 1983, pp. 509-533.
D.I. Siapkas, et al., "Structural and Compositional Characterization of High Energy Separation by Implantation of Oxygen Structures Using Infrared Spectroscopy," *J. Electrochem. Soc.*, Sep. 1996, vol. 143, No. 9, pp. 3019-3032.
V.A. Yakovlev, et al., "FTIR Dosimetry Mapping of as-Implanted SIMOX Wafers," *IEEE International SOI Conference*, Oct. 2001, pp. 39-40.
V.A. Yakovlev, et al., "FTIR Reflectance Characterization of SIMOX Buried Oxide Layers," *SPIE Conference on Optical Diagnostic Methods for Inorganic Transmissive Materials*, San Diego, CA, Jul. 1998, SPIE vol. 3425, pp. 2-9.

*Primary Examiner* — Gregory J Toatley
*Assistant Examiner* — Rebecca C Slomski
(74) *Attorney, Agent, or Firm* — Bruce P. Watson

(57) ABSTRACT

Methods and apparatus for measuring ion implant dose in a material provide for: measuring a reflection spectrum through an implantation surface of the material, the implantation surface having been subjected to an ion implantation process to create a material layer from the implantation surface to a depth within the material and a layer of weakness below the material layer; storing magnitudes of the reflection spectrum as a function of respective wavelengths of incident light on the implantation surface; and computing an ion implant dose used during the ion implantation process based on comparisons of at least two magnitudes of the reflection spectrum at least two corresponding wavelengths of the incident light.

19 Claims, 6 Drawing Sheets

METHODS AND APPARATUS FOR MEASURING ION IMPLANT DOSE

BACKGROUND

The present invention relates to the measurement of the ion implant dose in a material, such as a semiconductor material.

Knowing the actual ion implant dose in a material may be advantageous in the manufacture of various products, such as to test process variation, improve yield, monitor product quality, etc. The ability to measure ion implant dose may also be advantageous in the design of new products and systems, such as in the development of semiconductor-on-insulator (SOI) structures.

The ways to produce SOI structures include ion-implantation methods, such as those disclosed in U.S. Pat. No. 7,176,528. Such steps include: (i) exposing a silicon wafer surface to hydrogen ion implantation to create a bonding surface; (ii) bringing the bonding surface of the wafer into contact with a glass substrate; (iii) applying pressure, temperature and voltage to the wafer and the glass substrate to facilitate bonding therebetween; (iv) cooling the structure to a common temperature; and (v) separating the glass substrate and a thin layer of silicon from the silicon wafer.

In order to develop and/or manufacture such SOI structures, it may be desirable to measure the actual ion implant dose of the donor semiconductor (e.g., silicon) wafer. There are a number of existing techniques to obtain an indication of ion implant dose. For example, Secondary Ion Mass Spectrometry (SIMS) is a technique used in materials science and surface science to analyze the composition of solid surfaces and thin films by sputtering the surface of the specimen with a focused primary ion beam and collecting and analyzing ejected secondary ions. These secondary ions are measured with a mass spectrometer to determine the elemental, isotopic, or molecular composition of the surface. SIMS is not a completely adequate approach at least because it is a destructive test and measures only a small area of the sample.

Alternative approaches include in-situ dose monitors, which are used inside the implanter apparatus. Such in-situ dose monitors are also inadequate because they only provide an average ion dose that is presumed to have been implanted. In-situ dose monitors, however, do not measure or compute actual dose in the sample and they are not capable of detecting any non-uniformity or other variations in the implant dose across the sample. An existing implanter equipment manufacturer has developed a measurement and mapping tool based on a single wavelength or narrow wavelength range reflectivity measurement. Such a system is described in U.S. Patent Application Publication No. 2005/0112853, however, the system requires a baseline measurement before implant, which is undesirable. A further alternative approach employs a four-point probe to extract dose information based on resistivity measurements. The measurements, however, are affected by material resistivity, which can vary greatly, and are considered destructive due to the fact that the process requires contacting the sample with the probe.

Several carrier illumination techniques have been described for measurement of dopant profiles after ion implantation during semiconductor processing for making integrated circuits. However, these techniques use pulsed laser illumination (single wavelength) to create carriers and separate probe beams to measure reflectivity. Thus, in most cases such techniques are unable to distinguish between variations in implant dose and implant energy.

For the reasons discussed above, none of the aforementioned techniques and processes for measuring ion implant dose has been satisfactory, such as in the context of manufacturing SOI structures. Thus, there is a need in the art for new methods and apparatus for measuring ion implant dose.

SUMMARY

Methods and apparatus for measuring ion implant dose in a material provide for: measuring a reflection spectrum through an implantation surface of the material, the implantation surface having been subjected to an ion implantation process to create a material layer from the implantation surface to a depth within the material and a layer of weakness below the material layer; storing magnitudes of the reflection spectrum as a function of respective wavelengths of incident light on the implantation surface; computing an ion implant dose used during the ion implantation process based on comparisons of at least two magnitudes of the reflection spectrum at least two corresponding wavelengths of the incident light; and displaying the computed ion implant dose on a user-viewable medium.

The step of computing the ion implant dose used during the ion implantation process may include determining a peak-to-valley difference between at least one local maximum magnitude of the reflection spectrum and at least one local minimum magnitude of the reflection spectrum. The local maximum and minimum magnitudes of the reflection spectrum may be selected at respective wavelengths at which the material is sufficiently transparent to the incident light to permit the incident light to reach the layer of weakness below the material layer, reflect and exit the material for detection.

The step of computing the ion implant dose used during the ion implantation process may include computing a normalized peak-to-valley difference by dividing the peak-to-valley difference by a magnitude of the reflection spectrum that is not substantially affected by the ion implant dose. There are a number of ways in which this may be carried out as will be discussed later in this description.

The ion implant dose may then be computed as a function of the normalized peak-to-valley difference. This may be achieved by establishing a relationship between the ion implant dose and the normalized peak-to-valley difference. Such a relationship may be linear or nonlinear, but is preferably monotonic. Establishing monotonic relationship may include calibrating a known ion implant dose with the associated measured normalized peak-to-valley difference.

The methods and apparatus may further provide for: repeating the steps of measuring the reflection spectrum, storing magnitudes of the reflection spectrum, and computing the ion implant dose for a plurality of locations across the implantation surface of the material; and displaying the computed ion implant dose, including variations thereof, across the implantation surface of the material on the user-viewable medium.

Other aspects, features, advantages, etc. will become apparent to one skilled in the art when the description herein is taken in conjunction with the accompanying drawings.

BRIEF DESCRIPTION OF THE DRAWINGS

For the purposes of illustrating the various features disclosed herein, there are shown in the drawings forms that are presently preferred, it being understood, however, that the invention is not limited to the precise arrangements and instrumentalities shown.

DETAILED DESCRIPTION

Figure 1:
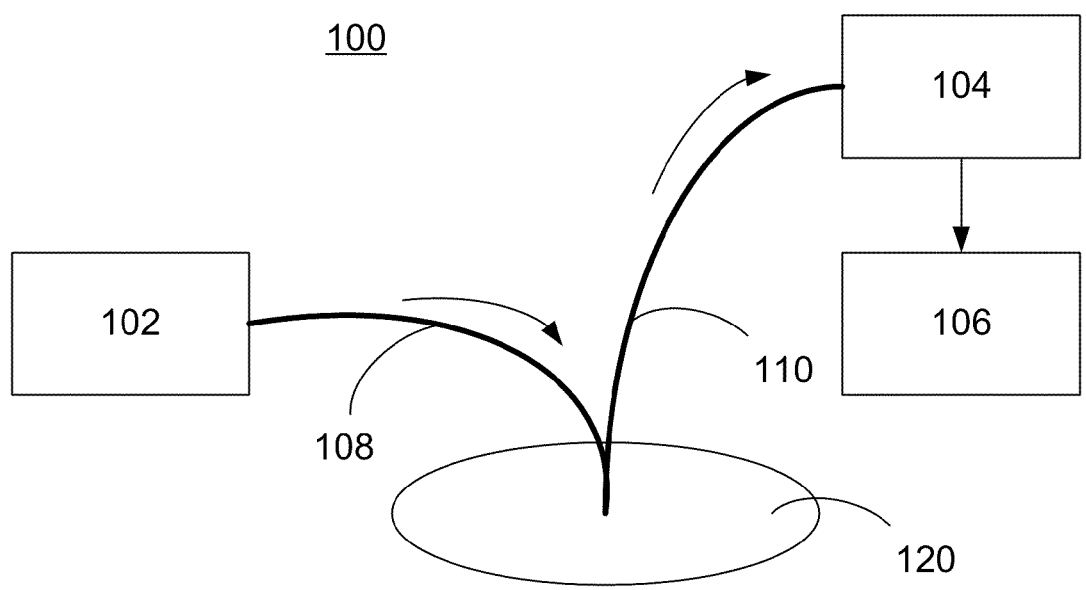
FIG. 1 is a block diagram illustrating an apparatus for measuring the ion implant dose of a material sample in accordance with one or more embodiments disclosed herein.

With reference to the drawings, wherein like numerals indicate like elements, there is shown in FIG. 1 an implant dose measurement apparatus 100 in accordance with one or more embodiments disclosed herein. The apparatus 100 operates to measure the ion implant dose of a sample piece of material 120, which may be a semiconductor wafer, such as a silicon wafer. The apparatus 100 includes a source of light 102, a spectrometer 104, and a computing system 106. Incident light is delivered from the source of light 102 to the sample 120 by way of an appropriate structure, such as a length of fiber optic material 108, and reflected light is collected and transmitted to the spectrometer 104 by way of a further structure, such as another length of fiber optic material 110. The computing system 106 includes a processor capable of running computer executable code, which is set up to compute the implant dose of the sample based on the reflected light collected and transmitted to the spectrometer 104. The computed ion implant dose may be provided to a user of the apparatus 100 by way of a display means within the computing system 106, such as a computer screen, a print-out, etc.

Before discussing further details of the apparatus 100, a discussion will first be provided as to an exemplary context within which the sample 120 may be found and certain processing that may have been carried out thereon. For purposes of discussion, the methods and apparatus described herein may be in the context of the development and/or manufacture of SOI structures. The SOI structures have suitable uses in connection with fabricating thin film transistors (TFTs), e.g., for display applications, including organic light-emitting diode (OLED) displays and liquid crystal displays (LCDs), integrated circuits, photovoltaic devices, etc.

To date, the semiconductor material most commonly used in SOI structures has been silicon. Such structures have been referred to in the literature as silicon-on-insulator structures and the abbreviation "SOI" has been applied to such structures. SOI technology is becoming increasingly important for high performance thin film transistors, solar cells, and displays, such as, active matrix displays. SOI structures may include a thin layer of substantially single crystal silicon on an insulating material.

The references to SOI structures herein are made to facilitate the explanation of the embodiments described herein and are not intended to, and should not be interpreted as, limiting the claims in any way. The SOI abbreviation is used herein to refer to semiconductor-on-insulator structures in general, including, but not limited to, semiconductor-on-glass (SOG) structures, silicon-on-insulator (SOI) structures, and silicon-on-glass (SiOG) structures, which also encompasses silicon-on-glass-ceramic structures. As used herein, SOI may also encompass semiconductor-on-semiconductor structures.

Figure 2:
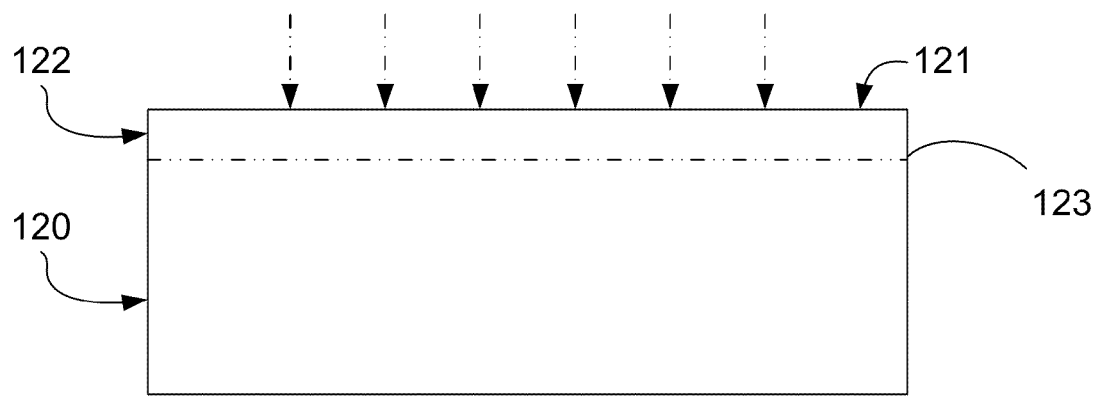
FIG. 2 is a block diagram illustrating an intermediate structure useful in producing a semiconductor-on-insulator product that may be the subject of the material under measurement in the apparatus of FIG. 1.

With reference to FIG. 2, a donor semiconductor wafer 120 may be used in the production of, or development of, an SOI device. In the context of the embodiments discussed herein, the donor semiconductor wafer 120 may be the sample material from which a computation of the ion implant dose is sought. Again, however, the sample material being semiconductor is only for example, and the implant dose measurement apparatus 100 and/or other methods and apparatus described herein may operate on other materials.

A donor semiconductor wafer 120 may have been prepared, such as by polishing, cleaning, etc. to produce a relatively flat and uniform implantation surface 121 suitable for bonding to a insulator substrate, such as another semiconductor material, glass or glass-ceramic substrate (not shown). For the purposes of discussion, the semiconductor wafer 120 may be a substantially single crystal Si wafer, although any other suitable semiconductor conductor material may be employed, such as the III-V, II-IV, II-IV-V, etc. classes of semiconductors. Examples of these materials include: silicon (Si), germanium-doped silicon (SiGe), silicon carbide (SiC), germanium (Ge), gallium arsenide (GaAs), GaP, and InP.

An exfoliation layer 122 is created by subjecting the implantation surface 121 to one or more ion implantation processes to create a weakened region below the implantation surface 121 of the donor semiconductor wafer 120. Although the embodiments of the present invention are not limited to any particular method of forming the exfoliation layer 122, one suitable method dictates that the implantation surface 121 of the donor semiconductor wafer 120 may be subject to a hydrogen ion implantation process to at least initiate the creation of the exfoliation layer 122 in the donor semiconductor wafer 120. The implantation energy may be adjusted using conventional techniques to achieve a general thickness of the exfoliation layer 122, such as between about 300-500 nm, although any reasonable thickness is within the scope of the invention. By way of example, hydrogen ion implantation may be employed, although other ions or multiples thereof may be employed, such as boron+hydrogen, helium+hydrogen, or other ions known in the literature for exfoliation. Again, any other known or hereinafter developed technique suitable for forming the exfoliation layer 122 may be employed.

Regardless of the nature of the implanted ion species, the effect of implantation on the exfoliation layer 122 is the displacement of atoms in the crystal lattice from their regular locations. When the atom in the lattice is hit by an ion, the atom is forced out of position and a primary defect, a vacancy and an interstitial atom, is created, which is called a Frenkel's pair. If the implantation is performed near room temperature, the components of the primary defect move and create many types of secondary defects, such as vacancy clusters, etc. Most of these types of defects are electrically active, and serve as traps for major carriers in the semiconductor lattice.

The resultant structure of the donor semiconductor wafer 120 is thus a material layer (the exfoliation layer 122) extending from the implantation surface 121 to a depth within the material and a layer of weakness 123 below the material layer. The implantation dose used in the formation of the layer of weakness 123 may be relatively high, much higher than doses used in later doping techniques. Thus, the layer of weakness 123 may be described as a mix of semiconductor (e.g., silicon) and hydrogen. Also, the layer of weakness 123 also includes several types of defects that are unique to, for example, situations where heavy dose implantation of hydrogen into silicon has been carried out. For example, the defects may include hydrogen filled bubbles, hydrogen platelets, and hydrogenated vacancy clusters.

With the above background concerning the structure of an exemplary material 120 (such as the aforementioned donor semiconductor wafer), the methods and apparatus (such as the apparatus 100) operate to measure the ion implant dose that caused the layer of weakness 123 of the material 120 and the other attendant structural characteristics thereof.

Figure 3A:
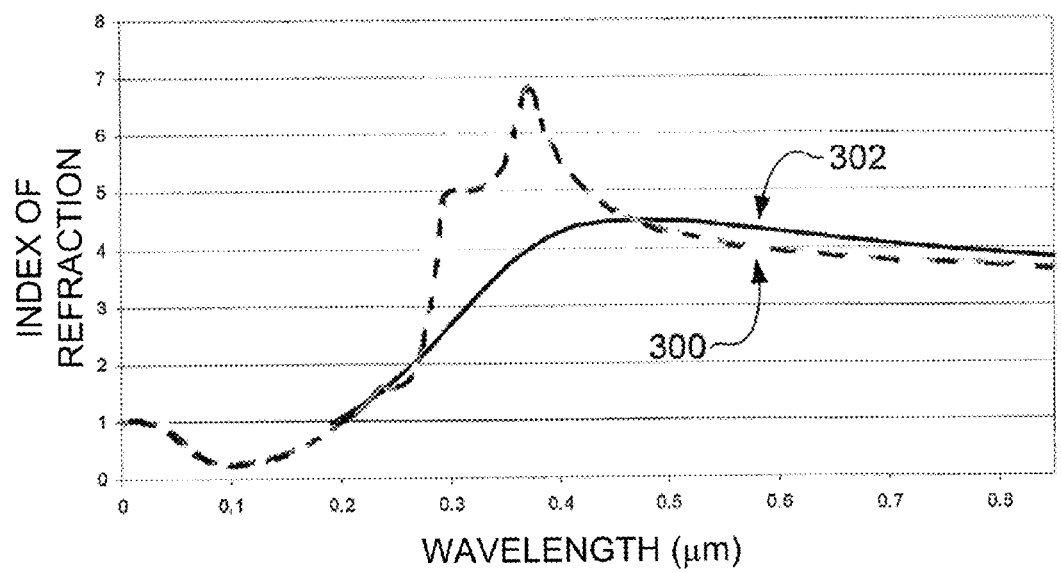
FIG. 3A illustrates the relationships between the index of refraction and the wavelength of incident light of the sample material with, and without, implanted ions.
Figure 3B:
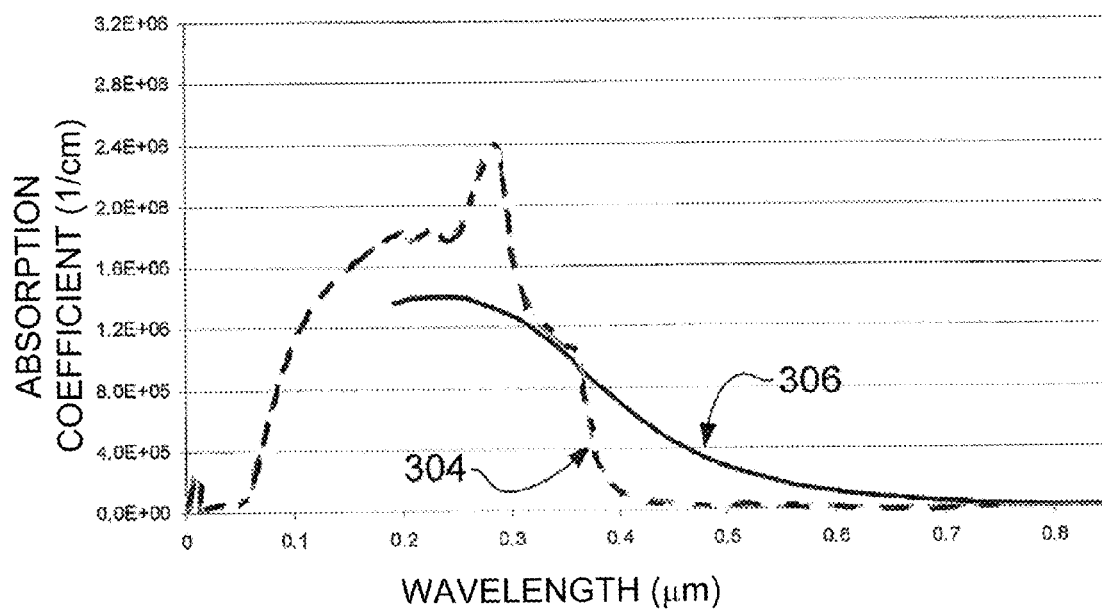
FIG. 3B illustrates the relationships between the absorption and the wavelength of incident light of the sample material with, and without, implanted ions.

With reference to FIGS. 3A and 3B, it is believed that the ion implanted semiconductor wafer 120 (silicon in this example) exhibits a significant change in the index of refraction in the layer of weakness 123 (as compared to the un-implanted regions of the wafer 120), which causes a reflection of at least some of the light incident on the implantation surface 121 by the source of light 102. Without limiting the scope of the claims herein, it is believed that such a difference in index is a key characteristic that leads to the ability to calculate the ion implant dose using spectroscopic reflectometry. FIG. 3A illustrates assumed relationships between the index of refraction (Y-axis in standard units) and the wavelength of incident light (X-axis in micrometers) of the semiconductor material 120 without implanted ions 300 and the layer of weakness 123, which includes implanted ions 302. The values shown in the graph of FIG. 3A were derived from known literature for crystalline and amorphous silicon wafers. FIG. 3B is a related graph illustrating the assumed relationships between the absorption coefficient (Y-axis in units of 1/cm) and the wavelength of incident light (X-axis in micrometers) of the semiconductor material without implanted ions 304 and with implanted ions 306. Again, values shown in the graph of FIG. 3B were derived from known literature for crystalline and amorphous silicon wafers. In practice, the actual values for the implanted semiconductor wafer 120 may be different from the values shown in FIGS. 3A-3B. It is assumed, however, that in practice the layer of weakness 123 will have an index of refraction and an absorption coefficient closer to 302, 306. It is also assumed that in practice, the exfoliation layer 122 will have values close to 300, 304. The methods and apparatus herein have been demonstrated through experiments and/or simulations to produce useful results, thereby justifying the above assumptions.

Within certain ranges of wavelength, such as above about 450 nm, the index of refraction of the ion implanted semiconductor material 120 (such as the layer of weakness 123) is higher than for the non-implanted regions of the semiconductor wafer 120, which may be single crystal material. It is believed, however, that the methods and apparatus herein only require that there is some difference in index of refraction (higher or lower) in the layer of weakness 123 as compared to the exfoliation layer 122. Notably, a wavelength range that meets the criteria for both (1) exhibiting some difference in the index of refraction between the layer of weakness 123 and the exfoliation layer 122 and (2) sufficient transparency, and thus may be suitable for analysis, may be from about 600 nm to 850 nm. In such a range of wavelengths, silicon semiconductor material is (1) sufficiently transparent to allow the light from the source of light 102 to penetrate through the exfoliation layer 122 and (2) has a sufficient difference on the index of refraction between the layer of weakness 123 and the exfoliation layer 122 to produce the interference needed for reflection (and thus resulting in the ability to measure ion dose). Although the index of refraction difference (between layer of weakness 123 and the exfoliation layer 122) is even greater in the 300-450 nm range, as shown in FIG. 3A, such wavelengths are not believed usable for analysis because silicon semiconductor material has very high absorption at those wavelengths. Thus, insufficient light would penetrate into the sample 120, be reflected, and escape back out of the sample 120 for detection by the probe. Other wavelengths, for example, in the infrared range, may be even more suitable for measurement if the refractive index difference and transmission are sufficient.

Although not intended to limit the scope of the claims, it has been assumed that the characteristic of the semiconductor wafer 120 that creates a suitable environment for measurement of the ion implant dose is the refractive index change in the layer of weakness 123 compared to the other material above and below. Another possibility, however, is that the ion implant species itself creates a change in the refractive index, thereby producing or contributing to the characteristics leading to sufficient light reflection.

Figure 4:
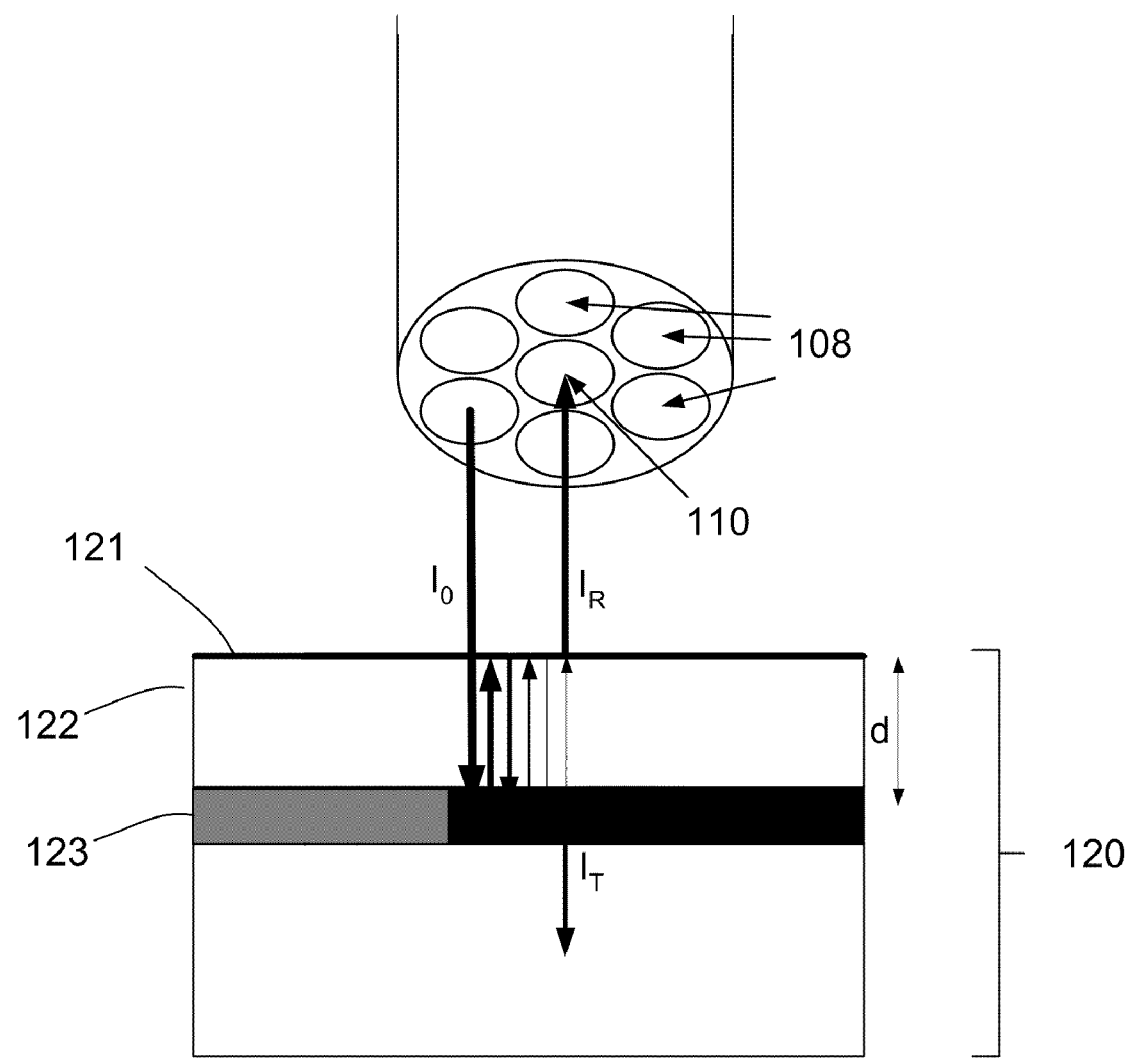
FIG. 4 is a more detailed schematic of a light providing and receiving component of the apparatus of FIG. 1.

With reference to FIG. 4, the incident light, Io, from the source of light 102 and the reflected light, Ir, from the sample 120 may be transmitted and received by way of an integrated fiber optic probe, which essentially implements the aforementioned lengths of fiber optic material 108, 110. Some light, It, passes through the layer of weakness 123 and is not reflected.

Figure 5:
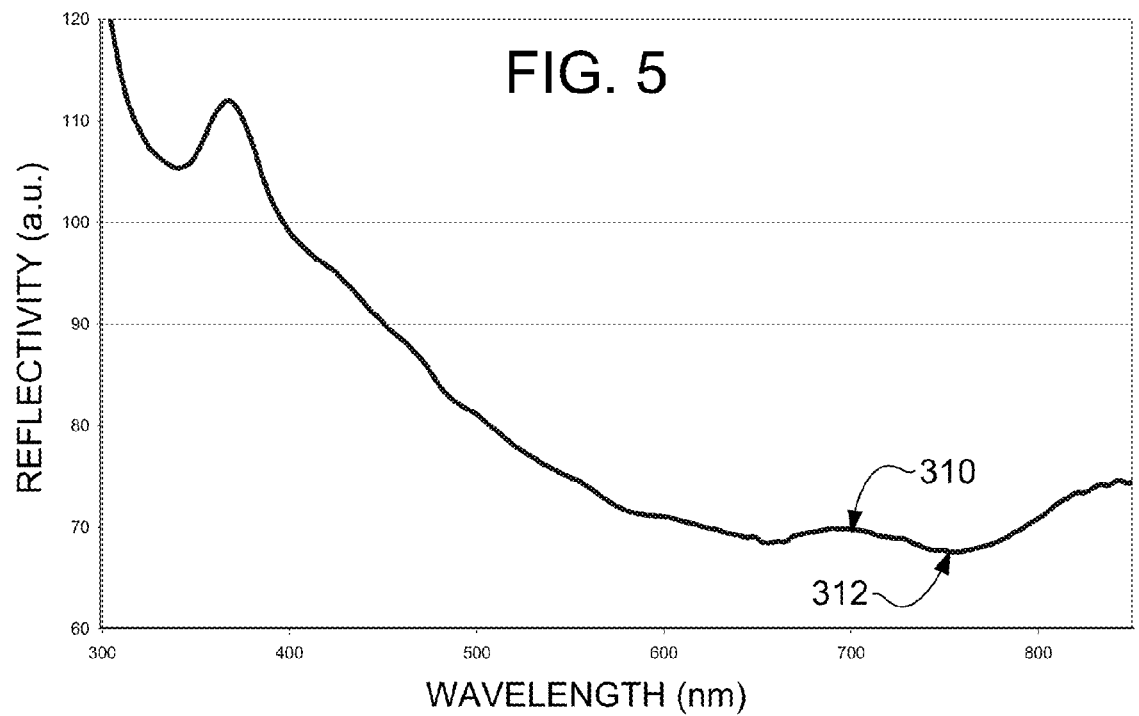
FIG. 5 is a graph illustrating a measured reflectance spectrum of a semiconductor material under measurement using the apparatus of FIG. 1.

The spectrometer 104 receives the reflected light Ir (from a particular area of the implantation surface 121 of the material 120) and processes same. As the incident light from the source 102 may be substantially white light, and therefore includes a plurality of wavelengths, a reflection spectrum at such area is established, such as is illustrated in FIG. 5. The computer readable memory of the computing system 106 operates to store magnitudes of the reflection spectrum as a function of the respective wavelengths of the incident light, Io. The processor within the computing system 106 is coupled to the computer readable memory and executes computer executable code, thereby causing the processor to compute the ion implant dose used during the ion implantation process based on the stored reflection spectrum.

More particularly, the ion implant dose is computed based on comparisons of at least two magnitudes of the reflection spectrum at least two corresponding wavelengths of the incident light. With reference to FIG. 5, which shows reflectivity (Y-axis in units of a.u.) versus wavelength (X-axis in units of nanometers), the two magnitudes of the reflection spectrum are respective local maxima and minima of the reflection spectrum. The local maximum magnitude 310 of the reflection spectrum occurs at an incident light wavelength of about 700 nm, while the local minimum magnitude 312 of the reflection spectrum occurs at an incident light wavelength of about 750 nm. The comparison of the local maximum magnitude 310 and the local minimum magnitude 312 may take the form of a mathematical difference (subtraction), producing a peak-to-valley difference value therebetween. Notably, the wavelengths at which the maxima and minima are found will depend on the thickness of the exfoliation layer 122. Thus, if desired, one may use the computed difference between the wavelengths of the maxima and minima locations to estimate the thickness of the exfoliation layer 122.

Notably, the local maximum and minimum magnitudes 310, 312 of the reflection spectrum are selected at respective wavelengths at which the material 120 is sufficiently transparent to the incident light, Io, to permit the incident light to reach the layer of weakness 123 and reflect back to the fiber optic probe. As discussed in some detail above, and for example only, such wavelengths for a semiconductor material 120, such as silicon, may be selected from between about 500 nm to about 1000 nm; more particularly between about 600 nm to about 850 nm; or still more particularly between about 650 nm to about 800 nm. Those skilled in the art will understand from the disclosure herein that the useful ranges within which to select the maxima and minima will depend on the type of material of the wafer 120, the transparency of same, the implantation parameters, etc.

Computing the ion implant dose used during the ion implantation process may also include computing a normalized peak-to-valley difference. The normalization process may be carried out by the computing system 106 and may be used to cancel errors caused by the non-ideal characteristics of the source of light 102.

The normalized peak-to-valley difference may be computed using a number of different approaches. One way is to divide the peak-to-valley difference by a magnitude of the reflection spectrum that is not substantially affected by the ion implant dose. For example, the magnitude of the reflection spectrum that is not substantially affected by the ion implant dose may occur at a lower wavelength than both of the respective wavelengths at which the local maximum and minimum magnitudes 310, 312 of the reflection spectrum are selected. By way of example, when the material is semiconductor (such as silicon) having the spectrum illustrated in FIG. 5, the magnitude of the reflection spectrum that is not substantially affected by the ion implant dose may be between about 100 nm and 500 nm; more particularly between about 250 nm and 400 nm; and still more particularly between about 325 nm and 375 nm. In general, the magnitude of the reflection spectrum that is not substantially affected by the ion implant dose may occur at any wavelength with high absorption in the exfoliation layer 122 (because the light will not reach the damaged layer 123). While a wavelength selected close to the local maximum and minimum magnitudes 310, 312 of the reflection spectrum is believed to be better for normalization (because variations in the light source will be more closely matched), the semiconductor material 120 will become more transparent at higher wavelengths.

In some circumstances, the above approach to computing the normalized peak-to-valley difference may produce less accurate results. Indeed, in some cases, the reflectivity measurement may be sensitive to small distance variations between the surface 121 of the semiconductor wafer 120 and the fiber probe 108, 110. Another approach to computing the normalized peak-to-valley difference that may be less prone to measurement error is to: (i) obtain the magnitude of the reflection spectrum that is not substantially affected by the ion implant dose (e.g., at the 350 nm wavelength) and the magnitude of the peak-to-valley signal, each as a function of distance between the surface 121 and the fiber probe 108, 110; (ii) use the magnitude of the reflection spectrum at 350 nm during the scan to estimate the distance (based on the previous step); and correct the peak-to-valley amplitude measured during the scan based on the estimated distance and an empirical function obtained from the first step.

Yet another approach to computing the normalized peak-to-valley difference is to: (i) average the signal amplitude at, or greater than, the wavelength range where the local maximum and minimum magnitudes 310, 312 are located (e.g., an average of all values between about 600-800 nm in the case of the spectrum of FIG. 5); and (ii) divide the peak-to-valley difference by the computed average.

Figure 6:
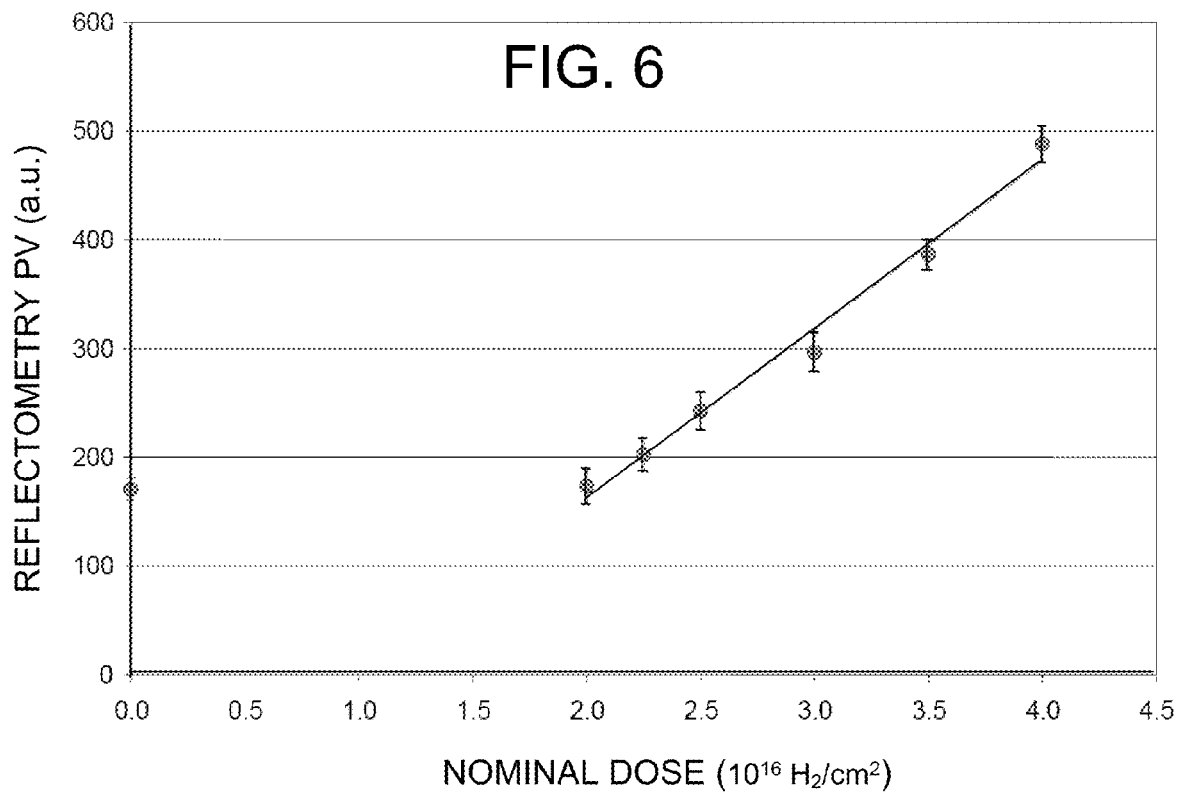
FIG. 6 is a graph illustrating a relationship between one or more portions of the reflectance spectrum of a semiconductor material under measurement and the ion implant dose thereof.

The ion implant dose may be computed as a function of the normalized peak-to-valley difference. This computation may be computed mathematically (and thus by the computing system 106) by establishing a relationship between the ion implant dose and the normalized peak-to-valley difference. Such a relationship may be linear or nonlinear, but is preferably monotonic. This may be accomplished by calibrating a known ion implant dose (such as that specified by persons implanting one or more wafers 120) with the associated measured normalized peak-to-valley difference. The calibration improves as the number of samples 120 increases and as the number of measurements of a given sample 120 are also increased. One approach is to take an average of measurements of the peak-to-valley difference (or even better the normalized peak-to-valley difference) of different areas on each wafer 120, and use such average for calibration. A monotonic function may then be readily established between the known ion implant dose (or doses) and the average peak-to-valley difference (or the normalized peak-to-valley difference). As illustrated in FIG. 6, which shows reflectometry peak-to-valley difference (Y-axis in units of a.u.) versus nominal dose (X-axis in units of $10^{16}$ $H_2/cm^2$), the relationship between the peak-to-valley difference (or the normalized peak-to-valley difference) along the Y-axis and the nominal dose (in $10 \times 16$ $H_2/cm^2$) along the X-axis using the above process are highly correlated. Each of the error bars indicates the standard deviation of all values measured on each of a number of samples 120 during experimentation.

Once the above steps in the process are carried out so that a relationship between the peak-to-valley difference (or the normalized peak-to-valley difference) and the nominal dose is obtained, measurements of unknown samples 120 may be carried out, using the aforementioned steps of measuring the reflection spectrum, storing magnitudes of the reflection spectrum, and computing the ion implant dose for a plurality of locations across the material 120. The computed ion implant dose, including variations thereof, across the implantation surface of the material may be displayed on the user-viewable medium.

Figure 7:
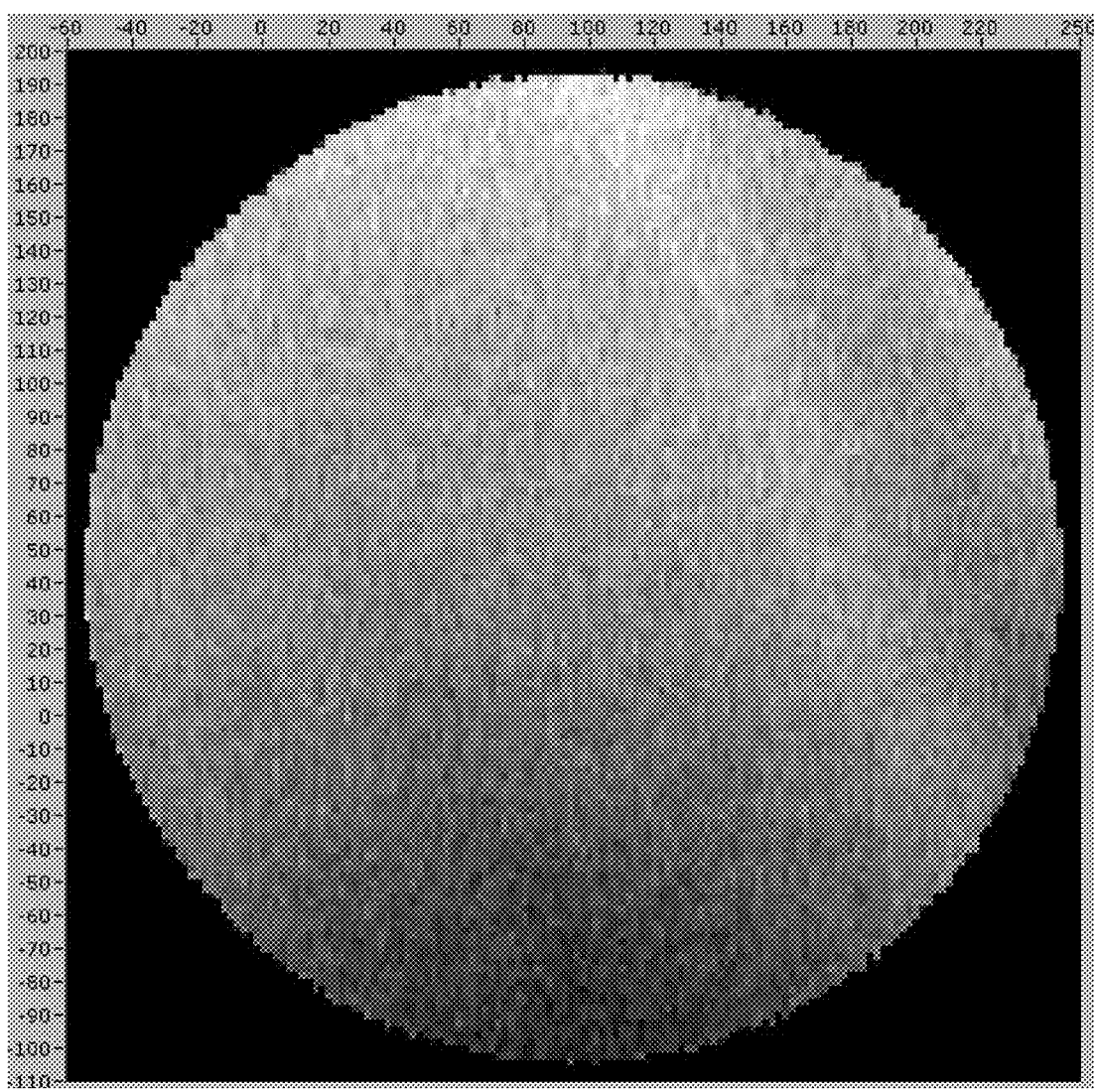
FIG. 7 is a graph illustrating experimental results using the apparatus of FIG. 1.

With reference to FIG. 7, an experiment was carried out using a silicon semiconductor wafer that had been implanted with hydrogen ions in a manner consistent with the techniques described above. The silicon semiconductor wafer measured 300 mm in diameter and was scanned using an apparatus consistent with that described above and shown in FIG. 1. The illustrated dose map includes distance in mm along each of the Y-axis and X-axis. The color/grayscale of the illustrated measured dose ranges from about $4*10^{16}$ $H_2/cm^2$ at the bottom of the wafer to about $5*10^{16}$ $H_2/cm^2$ at the top of the wafer with many variations therebetween.

Figure 8:
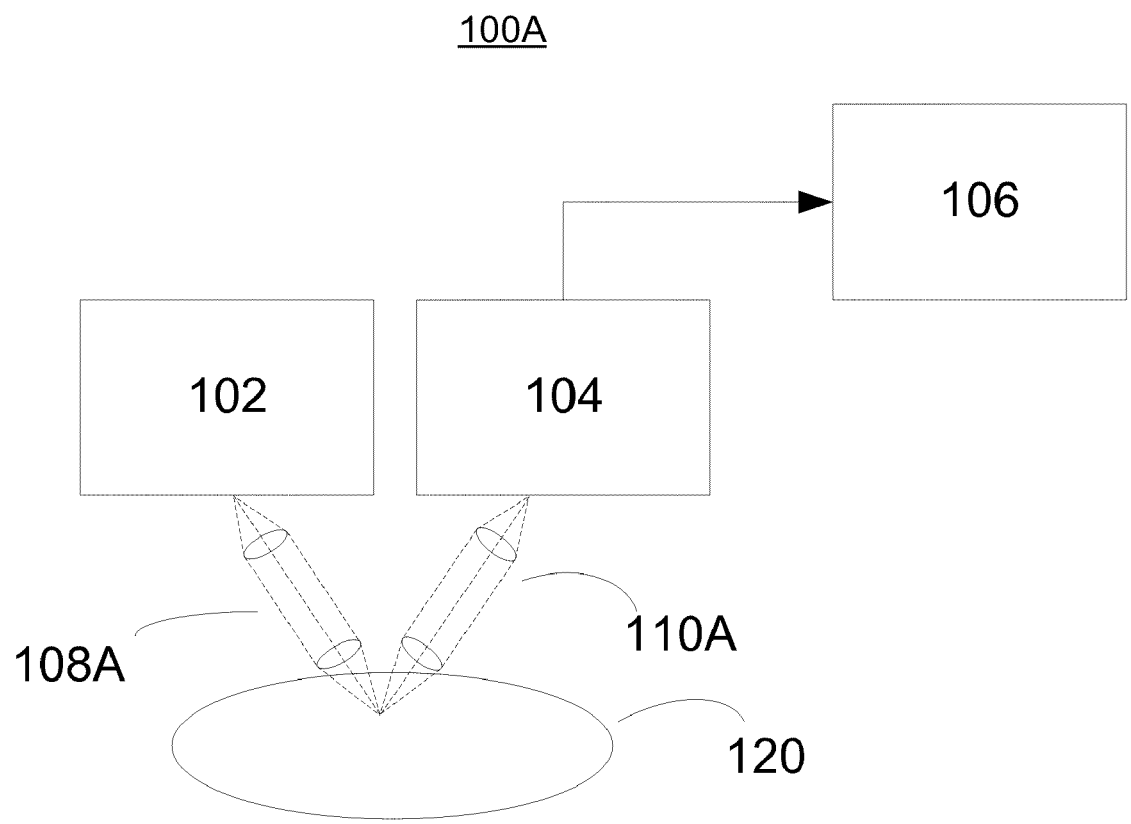
FIG. 8 is a block diagram illustrating an alternative apparatus for measuring the ion implant dose of a material sample in accordance with one or more embodiments disclosed herein.

With reference to FIG. 8, and in accordance with an alternative embodiment, an implant dose measurement apparatus 100A may also operate to measure the ion implant dose of a sample semiconductor wafer 120. Similarly numbered elements of the apparatus 100A may operate as described above with respect to FIG. 1. Unlike the apparatus 100 of FIG. 1, which employs fiber optics, the apparatus 100A includes free-space optics 108A, 110A for providing incident light to, and receiving light from, the wafer 120. Different portions of the wafer 120 may be measured by either moving the light source 102 and spectrometer 104 with respect to the wafer 120 (which may be challenging to maintain proper light focus), or moving the wafer 120 with respect to a stationary light source 102 and spectrometer 104. In this embodiment, the free-space optics 108A, 110A are angled such that proper measurement of reflected light by the spectrometer 104 may be achieved. In alternative embodiments, the free-space optics 108A, 110A may be at other transverse orientations that require a beam splitter and/or additional focusing lenses. In many other respects, the apparatus 100A operates substantially the same as the apparatus 100 of FIG. 1.

Although the embodiments herein have been described with reference to particular features, it is to be understood that these embodiments are merely illustrative of the principles and applications thereof. It is therefore to be understood that numerous modifications may be made to the illustrative embodiments and that other arrangements may be devised without departing from the scope of the appended claims.

The invention claimed is:

1. A method of measuring ion implant dose in a material, comprising:
    measuring a reflection spectrum through an implantation surface of the material, the implantation surface having been subjected to an ion implantation process to create a material layer from the implantation surface to a depth within the material and a layer of weakness below the material layer;
    storing magnitudes of the reflection spectrum as a function of respective wavelengths of incident light on the implantation surface;
    computing an ion implant dose used during the ion implantation process based on comparisons of at least two magnitudes of the reflection spectrum at least two corresponding wavelengths of the incident light; and
    displaying the computed ion implant dose on a user-viewable medium.

2. The method of claim 1, wherein the local maximum and minimum magnitudes of the reflection spectrum are selected at respective wavelengths at which the material is sufficiently transparent to the incident light to permit the incident light to reach the layer of weakness below the material layer, reflect, and exit the material.

3. The method of claim 2, wherein:
    the material is semiconductor; and
    the respective wavelengths at which the local maximum and minimum magnitudes of the reflection spectrum are selected are between about 500 nm to about 1000 nm.

4. The method of claim 3, wherein the respective wavelengths are between about 600 nm to about 850 nm; or between about 650 nm to about 800 nm.

5. The method of claim 2, further comprising estimating a thickness of the exfoliation layer as a function of the computed difference between the respective wavelengths at which the local maxima and local minima are located.

6. The method of claim 2, wherein the step of computing the ion implant dose used during the ion implantation process includes computing a normalized peak-to-valley difference by dividing the peak-to-valley difference by a magnitude of the reflection spectrum that is not substantially affected by the ion implant dose.

7. The method of claim 6, wherein the magnitude of the reflection spectrum that is not substantially affected by the ion implant dose is determined at a lower wavelength than both of the respective wavelengths at which the local maximum and minimum magnitudes of the reflection spectrum are selected.

8. The method of claim 6, wherein the magnitude of the reflection spectrum that is not substantially affected by the ion implant dose is computed as an average of a plurality of values within a wavelength range that includes both the local maximum and minimum magnitudes of the reflection spectrum.

9. The method of claim 7, wherein at least one of:
    the material is silicon;
    the magnitude of the reflection spectrum that is not substantially affected by the ion implant dose is between about 100 nm and 500 nm; and
    the magnitude of the reflection spectrum that is not substantially affected by the ion implant dose is between about 250 nm and 400 nm, or between about 325 nm and 375 nm.

10. The method of claim 6, wherein the ion implant dose is computed as a function of the normalized peak-to-valley difference.

11. The method of claim 6, further comprising establishing a monotonic relationship between the ion implant dose and the normalized peak-to-valley difference.

12. The method of claim 11, wherein the step of establishing the monotonic relationship includes calibrating a known ion implant dose with the associated measured normalized peak-to-valley difference.

13. The method of claim 1, further comprising:
    repeating the steps of: measuring the reflection spectrum, storing magnitudes of the reflection spectrum, and computing the ion implant dose for a plurality of locations across the implantation surface of the material; and
    displaying the computed ion implant dose, including variations thereof, across the implantation surface of the material on the user-viewable medium.

14. The method of claim 1, wherein at least one of:
    the material is a semiconductor; and
    the semiconductor is taken from the group consisting of silicon (Si), germanium-doped silicon (SiGe), silicon carbide (SiC), germanium (Ge), gallium arsenide (GaAs), GaP, and InP.

15. A method of measuring ion implant dose in a material, comprising:
    measuring a reflection spectrum through an implantation surface of the material, the implantation surface having been subjected to an ion implantation process to create a material layer from the implantation surface to a depth within the material and a layer of weakness below the material layer;
    storing magnitudes of the reflection spectrum as a function of respective wavelengths of incident light on the implantation surface;
    determining a peak-to-valley difference between at least one local maximum magnitude of the reflection spectrum and at least one local minimum magnitude of the reflection spectrum, where the local maximum and minimum magnitudes of the reflection spectrum are selected at respective wavelengths at which the material is sufficiently transparent to the incident light to permit the incident light to reach the layer of weakness below the material layer, reflect, and exit the material;
    computing a normalized peak-to-valley difference by dividing the peak-to-valley difference by a magnitude of the reflection spectrum that is not substantially affected by the ion implant dose;
    computing the ion implant dose as a function of the normalized peak-to-valley difference; and
    displaying the computed ion implant dose on a user-viewable medium.

16. An apparatus, comprising:
    a spectrometer for measuring a reflection spectrum through an implantation surface of a material, the implantation surface having been subjected to an ion implantation process to create a material layer from the implantation surface to a depth within the material and a layer of weakness below the material layer;

a computer readable memory operating to store magnitudes of the reflection spectrum as a function of respective wavelengths of incident light on the implantation surface;

a processor coupled to the computer readable memory and operating to execute computer executable code causing the processor to execute actions, including:

computing an ion implant dose used during the ion implantation process based on comparisons of at least two magnitudes of the reflection spectrum at least two corresponding wavelengths of the incident light; and determining a peak-to-valley difference between at least one local maximum magnitude of the reflection spectrum and at least one local minimum magnitude of the reflection spectrum, where the local maximum and minimum magnitudes of the reflection spectrum are selected at respective wavelengths at which the material is sufficiently transparent to the incident light to permit the incident light to reach the layer of weakness below the material layer;

means for displaying the computed ion implant dose on a user-viewable medium.

17. The apparatus of claim 16, wherein the computer executable code causes the processor to execute further actions, including:

computing a normalized peak-to-valley difference by dividing the peak-to-valley difference by a magnitude of the reflection spectrum that is not substantially affected by the ion implant dose;

computing the ion implant dose as a function of the normalized peak-to-valley difference.

18. The apparatus of claim 17, wherein at least one of:

the computer executable code includes a monotonic relationship between the ion implant dose and the normalized peak-to-valley difference; and the monotonic relationship includes a predetermined calibration of a known ion implant dose with the associated measured normalized peak-to-valley difference.

19. The apparatus of claim 16, wherein the spectrometer, computer readable memory, processor, and computer executable code cooperate together to repeat: the measurement of the reflection spectrum, storage of magnitudes of the reflection spectrum, computation of the ion implant dose, and the display of the computed ion implant dose, including variations thereof, for a plurality of locations across the implantation surface of the material.

* * * * *